United States Patent [19]

Bott

[11] 4,380,631

[45] Apr. 19, 1983

[54] PREPARATION OF CAFFEINE

[75] Inventor: Kaspar Bott, Wachenheim, Fed. Rep. of Germany

[73] Assignee: BASF Aktiengesellschaft, Fed. Rep. of Germany

[21] Appl. No.: 359,839

[22] Filed: Mar. 19, 1982

[30] Foreign Application Priority Data

Apr. 7, 1981 [DE] Fed. Rep. of Germany ....... 3113880

[51] Int. Cl.$^3$ ............................................ C07D 473/12
[52] U.S. Cl. .................................... 544/275; 424/253
[58] Field of Search ................. 424/253; 544/267, 275

[56] References Cited

U.S. PATENT DOCUMENTS

| | | | |
|---|---|---|---|
| 2,509,084 | 5/1950 | Decker | 544/275 |
| 2,523,496 | 9/1950 | Campbell | 544/275 |
| 3,975,389 | 8/1976 | Arcadi et al. | 426/253 |
| 3,998,953 | 12/1976 | Konz et al. | 424/253 |

OTHER PUBLICATIONS

Ber 95, 1902–1909 (1962).
Kirk-Othmer, Encyclopedia of Chemical Technology, 2nd Edition, vol. 3, p. 916.

*Primary Examiner*—Nicholas S. Rizzo
*Attorney, Agent, or Firm*—Keil & Witherspoon

[57] ABSTRACT

Caffeine is prepared from theophylline, carbon monoxide and methanol.

2 Claims, No Drawings

PREPARATION OF CAFFEINE

The present invention relates to a novel process for the preparation of caffeine.

Caffeine is generally obtained industrially by reacting the sodium or potassium salt of theophylline with a methylating agent, preferably dimethyl sulfate or methyl chloride (Kirk-Othmer, Encyclopedia of Chemical Technology, 2nd edition, Volume 3, page 916). However, dimethyl sulfate has the disadvantage that it is very toxic, and special safety measures are necessary when handling it. It is true that this disadvantage is substantially overcome by using methyl chloride, but in both cases a relatively large molar excess of the methylating agent must be used to achieve a high caffeine yield. This means that a high proportion of the methyl chloride or dimethyl sulfate is lost from the caffeine synthesis by non-methylating hydrolysis to methanol. Moreover, the methyl chloride and dimethyl sulfate have to be produced in a separate stage from methanol and hydrogen chloride or, respectively, sulfuric acid.

It is an object of the present invention to provide a simpler process for the preparation of caffeine.

We have found that this object is achieved by a process for the preparation of caffeine wherein methanol and carbon monoxide are reacted with an alkali metal salt of theophylline.

The reaction can be represented by the following equation:

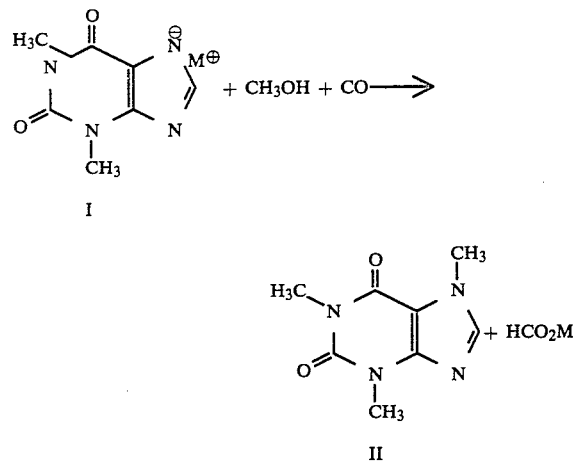

where M is an alkali metal atom.

Sodium formate, which is produced industrially from sodium hydroxide solution and carbon monoxide, is obtained in this caffeine synthesis and constitutes a further useful product.

Preferably, in the novel synthesis of caffeine, the sodium or potassium salt of theophylline is heated to 120°–170° C., preferably 130°–150° C., with carbon monoxide and an excess of methanol. The carbon monoxide pressure in the reaction vessel is advantageously 25–100 bar, preferably 40–60 bar.

In the reaction, according to the invention, of theophylline with methanol and carbon monoxide, some of the methanol used in excess reacts with the carbon monoxide, but the methyl formate thereby formed does not present any problems in the process, because methyl formate can also be used instead of the mixture of methanol and carbon monoxide for the methylation of theophylline. If methyl formate is used, it is possible to dispense with the addition of carbon monoxide entirely.

The noval process substantially simplifies the preparation of caffeine, and moreover gives a good yield of highly pure product.

The Examples which follow illustrate the invention further.

EXAMPLE 1

A mixture of 100 g of methanol and 22.6 g of the potassium salt of theophylline is heated at 140° C. in a 200 ml stirred autoclave under a continual CO pressure of 50 bar for 20 hours. The contents of the reactor are flushed into a distillation flask with methanol, and the methanol and methyl formate are distilled off. 29.5 g of a mixture of caffeine and potassium formate which, according to thin layer chromatography, contains only 0.6% of theophylline are obtained as a solid distillation residue. 19.2 g (97%) of caffeine can be extracted from the residue with ethyl acetate.

EXAMPLE 2

A mixture of 50 g of methanol, 50 g of methyl formate and 22.0 g of the potassium salt of theophylline is heated at 140° C. in a stirred autoclave for 20 hours. The mixture is worked up as described in Example 1 to give 29.7 g of a distillation residue composed of 18.7 g of caffeine, 0.18 g of theophylline and 10 g of potassium formate. The caffeine yield is 97.5%.

I claim:

1. A process for the preparation of caffeine which comprises reacting methanol and carbon monoxide with an alkali metal salt of theophylline at a temperature of from 120° to 170° C. and under a carbon monoxide pressure of from 25 to 100 bar.

2. A process for the preparation of caffeine which comprises: reacting an alkali metal salt of theophylline with methyl formate at a temperature of from 120° to 170° C.